United States Patent [19]

Hartig et al.

[11] Patent Number: 4,587,363

[45] Date of Patent: May 6, 1986

[54] CONTINUOUS PREPARATION OF OXYGEN-CONTAINING COMPOUNDS

[75] Inventors: Jürgen Hartig, Gruenstadt; Gunter Schuch, Ludwigshafen; Armin Stoessel, Frankenthal; Guenter Herrmann, Heidelberg; Arthur Brunner, Ludwigshafen; Peter Zehner, Ludwigshafen; Otto-Alfred Grosskinsky, Ludwigshafen, all of Fed. Rep. of Germany

[73] Assignee: BASF Aktiengesellschaft, Fed. Rep. of Germany

[21] Appl. No.: 639,325

[22] Filed: Aug. 10, 1984

[30] Foreign Application Priority Data

Aug. 10, 1983 [DE] Fed. Rep. of Germany ....... 3328771

[51] Int. Cl.$^4$ .............................................. C07C 45/33
[52] U.S. Cl. .................... 568/357; 568/358; 568/376; 568/836
[58] Field of Search ..................... 568/357, 376, 398.8, 568/399, 400, 836, 358

[56] References Cited

U.S. PATENT DOCUMENTS

| | | | |
|---|---|---|---|
| 2,684,984 | 7/1954 | Finch et al. | 568/357 |
| 3,530,185 | 9/1970 | Pugi | 260/586 |
| 3,546,303 | 12/1970 | Hornberger et al. | 568/836 |
| 3,671,588 | 6/1972 | Murray et al. | 568/357 |
| 4,491,674 | 1/1985 | Rieber et al. | 568/357 |

FOREIGN PATENT DOCUMENTS 0757513 8/1980 U.S.S.R. ............... 568/836

*Primary Examiner*—Werren B. Lone
*Attorney, Agent, or Firm*—Keil & Weinkauf

[57] ABSTRACT

Oxygen-containing compounds are prepared by oxidizing a hydrocarbon in the liquid phase with a gas containing molecular oxygen, at elevated temperatures and under superatmospheric pressure, by a continuous process in which the said gas is fed into the liquid reaction mixture, in a downward direction, at several points along the reaction zone via nozzle apertures, so that it emerges at each nozzle aperture with a velocity of from 0.01 to 1 m/sec in an amount of from 0.001 to 10 liters per second per nozzle aperture, and the said reaction mixture is brought into substantially uniform contact with the gas containing molecular oxygen, over the volume of the reaction zone.

5 Claims, No Drawings

CONTINUOUS PREPARATION OF OXYGEN-CONTAINING COMPOUNDS

The present invention relates to a continuous process for a preparation of oxygen-containing compounds by oxidizing a hydrocarbon in the liquid phase with a gas containing molecular oxygen, at elevated temperatures and under superatmospheric pressure, wherein the said gas is passed in at several points along the reaction zone via nozzle apertures in a downward direction.

The oxidation of hydrocarbons with gases containing molecular oxygen is frequently carried out industrially. The aim in such a procedure is to prevent the oxidation of the hydrocarbons from taking place in an uncontrolled manner, ensuring that the particular product desired is obtained, and to reduce the amount of by-products. An industrially important reaction of this type is the oxidation of cyclohexane to cyclohexanol or cyclohexanone. Such a process is described in, for example, German Pat. No. 1,287,575. In this process, cyclohexane is passed from above into a reaction zone, and a gas containing molecular oxygen is fed countercurrent to the cyclohexane. The reaction zone is divided into several zones by perforated sheets which do not cover the entire cross-section, the gas containing molecular oxygen being fed in below the perforated sheets, in a downward direction. Such a procedure does not permit molecular oxygen to be fed in uniformly and results, in particular, in non-uniform flow of the reaction mixture. Moreover, the procedure leads to the formation of pockets of oxygen-containing gas, which constitutes an explosion hazard and hence presents problems. In general, the procedure described there results in non-uniform contact with molecular oxygen.

It is an object of the present invention to provide a process for oxidizing hydrocarbons with a gas containing molecular oxygen, in which the oxidation takes place uniformly, high yields of the desired products are obtained, and the amount of by-products is minimized.

We have found that this object is achieved by a process for the continuous preparation of an oxygencontaining compound by oxidizing a hydrocarbon in the liquid phase with a gas containing molecular oxygen, at elevated temperatures and under superatmospheric pressure, the said gas being fed in at several points along the reaction zone via nozzle apertures in a downward direction, wherein the gas which contains molecular oxygen and is passed into the liquid reaction mixture emerges at each nozzle aperture at a velocity of from 0.01 to 1 m/sec in an amount of from 0.001 to 10 liters per second per nozzle aperture, and the said reaction mixture is brought into substantially uniform contact with the gas containing molecular oxygen, over the volume of the reaction zone.

The novel process has the advantages that it requires no mechanical means for effecting thorough mixing, and uniform distribution of molecular oxygen in the hydrocarbon being oxidized is achieved in a simple manner, that, in particular, a cohesive gas phase is not formed, and that the oxidation takes place uniformly, high yields of the desired products are obtained and the amount of by-products is reduced.

According to the invention, the starting materials used are hydrocarbons, in particular alkanes of 4 to 18 carbon atoms, cycloalkanes where the ring is of 5 to 12 carbon atoms, or alkyl-aromatics of 7 to 12 carbon atoms. In this process, alkanes are oxidized to fatty acids, e.g. butane to acetic acid, and toluene is oxidized to benzoic acid. The oxidation of cycloalkanes to the corresponding cycloalkanols or cycloalkanones is particularly important.

The oxidation is carried out using gases containing molecular oxygen. Advantageously, such gases contain from 5 to 30 vol % of molecular oxygen. The procedure is advantageously carried out at from 100° to 180° C. and under from 5 to 30 bar. The temperature and pressure are matched with one another so that the entire reaction takes place in the liquid phase.

The reaction is advantageously carried out in horizontal or, in particular, vertical reaction zones. The gas containing molecular oxygen is fed into the liquid hydrocarbon at several points along the reaction zone, through nozzle apertures, in a downward direction. An essential feature of the invention is that the said gas, which is passed into the liquid reaction mixture, emerges at each nozzle aperture at a velocity of from 0.01 to 1, in particular from 0.03 to 0.3, m/sec, in an amount of from 0.001 to 10, in particular from 0.1 to 1.0, liters per second per nozzle aperture. The nozzle apertures are distributed substantially uniformly over the volume of the reaction zone. This is achieved by, for example, arranging nozzle apertures along the reaction zone, at several points substantially equal distances apart, the said apertures being distributed uniformly over the cross-section of the reaction zone. The spacings along the reaction zone are advantageously from 0.5 to 3 times the diameter of the reaction zone, and are chosen in particular so that the molecular oxygen in the gas bubbles rising from the preceding feedpoint is not completely consumed, for example from 60 to 90% of the initial content being consumed. This results in contact between the hydrocarbon being oxidized and the gas containing molecular oxygen being substantially uniform over the volume. Of course, substantially the same amount of gas is fed in through each nozzle aperture. The incomplete reaction of the oxygen also results in an equilibration of the $O_2$ concentration in the reactor. The final $O_2$ concentration (concentration in the exit gas) is established in the uppermost part of the reactor.

When a gas containing molecular oxygen is fed in so that it emerges from the nozzle aperture at a velocity of from 0.01 to 1 m/sec in an amount of from 0.001 to 10 liters per second per nozzle aperture, the nozzle apertures pointing downward, bubbles are obtained which have a diameter of $\geq 10$ mm, e.g. from 10 to 100 mm, and which are initially larger than the equilibrium bubbles but break up along the reaction zone to give such bubbles. Equilibrium bubbles are bubbles which are formed at a certain distance from the nozzle aperture as a result of division or coalescence processes; for example, for the cyclohexane/air system, the mean diameter of the equilibrium bubbles is from 1 to 10 mm.

In an industrial embodiment, each exit point is supplied uniformly with oxygen-containing gas via feed lines possessing a large number of very small holes which result in a defined pressure loss. The said gas emerges from each fine hole into a space which is closed above and open below and which has dimensions such that, with the amounts of gas used, the gas passing into the reaction medium emerges at the velocity stated above. For example, an oxygen-containing gas is fed through a fine hole into an extension which is open below and, apart from the fine hole, closed above. The extension can be cylindrical, conical, rectangular, square, trumpet-shaped or bell-shaped. The lower edge of the extension may furthermore be serrated or oblique. The geometric dimensions of this extension depend on the exit velocity to be maintained at the nozzle aperture and the amount of gas emerging, and can easily be calculated using the data given.

Advantageously, the reaction zone contains chambers, i.e. is divided into sections, in order to avoid back-mixing. This is achieved in the case of horizontal reaction zones by means of overflows or separating walls with passages, and in the case of vertical reaction zones by means of perforated sheets incorporated at equal distances apart. Furthermore, it has proven particularly advantage ous in the case of vertical reaction zones if the hydrocarbon being oxidized and the gas containing molecular oxygen are fed upward cocurrent with one another. It has also been found to be useful if a cohesive gas phase does not form in the reaction zone.

The process according to the invention may be illustrated by the oxidation of cycloalkanes to a mixture of cycloalkanols, cycloalkanones and cycloalkyl hydroperoxides, for example the oxidation of cyclohexane. The reaction zone used is a vertical one which is divided into chambers by means of perforated sheets arranged at equal distances. The perforated sheets advantageously have a free cross-section of from 3 to 20%, in particular from 5 to 10%. Above each perforated sheet, nozzles are arranged uniformly over the cross-section, the feed apertures being provided with extensions whose apertures point downwards. Cyclohexane is passed upward through the reaction zone. At the same time, a gas containing molecular oxygen, for example having an oxygen content of from 1 to 30 vol %, is fed through each nozzle aperture in an amount of from 0.001 to 10 liters/sec, the exit velocity at the nozzle aperture being maintained at from 0.01 to 1 m/sec. The reaction is carried out at from 120 to 180° C. under from 5 to 30 bar. The amounts of oxygen-containing gas and cyclohexane which are fed in are matched with one another so that the exit gas emerging from the reaction zone contains not more than 2.5, e.g. from 0.1 to 1.5, vol % of molecular oxygen.

Cycloalkanols and cycloalkanones obtained by the process of the invention are starting materials for the preparation of fiber raw materials, such as dicarboxylic acids or lactams.

The Examples which follow illustrate the process according to the invention. Examples 1, 2, 3, 5, 7, 8, 10, 11 and 14 are comparative examples.

EXAMPLES 1 TO 7

155 kg/hour of cyclohexane containing 0.3 ppm of cobalt in the form of cobalt ethylhexanoate are fed from below into a vertical cylindrical reactor which has a capacity of 100 liters and a ratio of height to diameter of 2 and does not contain any baffles. At the same time, 5 m3 (S.T.P.)/ hour of air are fed in, the methods for doing this being described below. The reaction is carried out at 165° C. and under 15 bar. Exit gas and liquid reaction mixture are removed at the upper end of the reactor, the said reaction mixture is washed with water and sodium hydroxide solution, and the mixture of cyclohexanol and cyclohexanone is then isolated by distillation.

EXAMPLE 1

Air is fed in via an inserted tube of 10 mm diameter. The air emerges at a velocity of 1.75 m/sec, the mean bubble diameter is from 10 to 40 mm, and the yield of cyclohexanol/cyclohexanone is 74 mol %.

EXAMPLE 2

Air is fed in via a perforated tray which has 16 holes which are of 2 mm diameter and are distributed uniformly over the cross-sec-tion. The air emerges at a velocity of 2.75 m/sec, the mean bubble diameter is from 1 to 10 mm and the yield of cyclohexanol/cyclohexanone is 75.5 mol %.

EXAMPLE 3

Air is fed in via a perforated tray which has 155 holes which are of 0.5 mm diameter and are distributed uniformly over the cross-section. The air emerges at a velocity of 4.55 m/sec, the mean bubble diameter is from 1 to 6 mm, and the yield of cyclohexanol/cyclohexanone is 74.5 mol %.

EXAMPLE 4

Air is fed in downward through 16 nozzles distributed over the cross-section, each nozzle terminating in an extension which has a diameter of 10 mm and a height of 30 mm. The velocity with which the air emerges at the feed point and enters the liquid is 0.11 m/sec, the mean bubble diameter when the bubble emerges from the nozzle aperture is greater than 10 mm, and the yield of cyclohexanol/cyclohexanone is 76 mol %.

EXAMPLE 5

Air is fed in via an inserted tube of 10 mm diameter. In addition, the reactor is equipped with a disk stirrer operated at 1,000 rpm and circuit breakers. The air emerges at a velocity of 1.75 m/sec, the mean bubble diameter is from 1 to 2 mm, and the yield of cyclohexanol/cyclohexanone is 74.5 mol %.

EXAMPLE 6

Air is fed in at two levels 30 cm apart, through 16 holes in each case, as described in Example 4. The air emerges at a velocity of 0.055 m/sec, the mean bubble diameter when the bubble emerges from the nozzle aperture is greater than 10 mm, and the yield of cyclohexanol/cyclohexanone is 77 mol %.

EXAMPLE 7

Air is fed in via a two-material jet nozzle having an annular gap of 0.1 mm for the air. The air emerges at a velocity of 65.9 m/sec, the mean bubble diameter is less than 1 mm, and the yield of cyclohexanol/cyclohexanone is 73 mol %.

The yields are based in each case on cyclohexane converted.

EXAMPLE 8

The procedure described in Example 1 is followed, except that the temperature is maintained at 145 °C. The oxygen content of the exit gas is 3–4 vol %. The reaction does not proceed in a stable manner.

EXAMPLE 9

The procedure described in Example 4 is followed, and the temperature is maintained at 145° C. The oxygen content of the exit gas is 0.2 vol %. The reaction proceeds in a stable manner.

EXAMPLES 10 TO 13

155 kg/hour of cyclohexane containing 0.3 ppm of cobalt in the form of cobalt ethylhexanoate are fed from below into a cylindrical reactor which has a capacity of 100 liters and a ratio of height to diameter of 15 and does not contain any baffles. At the same time, 5 m$^3$(S.T.P.)/hour of air are fed in, the methods for doing this being described below. The reaction is carried out at 165° C. and under 15 bar.

The various procedures according to Examples 10 to 13, and the results obtained, are described below.

EXAMPLE 10

Air is fed in via an inserted tube of 10 mm diameter. The air emerges at a velocity of 1.75 m/sec, the mean bubble diameter when the bubble emerges from the nozzle aperture is from 10 to 40 mm, and the yield of cyclohexanol/cyclohexanone is 69 mol %.

EXAMPLE 11

Air is fed in via a perforated tray which has 16 holes which are of 2 mm diameter and are distributed uniformly over the cross-section. The air emerges at a velocity of 2.75 m/sec, the mean bubble diameter is from 1 to 10 mm, and the yield of cyclohexanol/cyclohexanone is 71 mol %.

EXAMPLE 12

The air is fed in downward via 7 nozzles which are arranged 40 cm apart along the reactor and are staggered when viewed from below in cross-section, the nozzles having extensions which possess a diameter of 10 mm and a height of 30 mm. The air emerges at a velocity of 0.22 m/sec, the mean bubble diameter when the bubble emerges from the nozzle aperture is greater than 10 mm, and the yield of cyclohexanol/cyclohexanone is 73 mol %.

EXAMPLE 13

The procedure described in Example 12 is followed. The cylindrical reactor is divided into chambers by means of separating sheets between the individual nozzles along the reactor. The separating sheets each contain 16 holes of 2 mm diameter. The free cross-section, including the annular gap at the cylindrical part of the reactor, is 2%. Each of the separating sheets is located below the nozzles for the air feed. The air emerges at a velocity of 0.22 m/sec, the mean bubble diameter is greater than 10 mm, and the yield of cyclohexanol/cyclohexanone is 78 mol %.

EXAMPLE 14

The oxidation is carried out in an oxidation system consisting of three reactors in series (volume of each reactor 40 m$^3$, height 16 m, diameter 1.8 m), a working up section (removal of acids by washing with water and extraction, and neutralization with sodium hydroxide solution) and a distillation section (isolation of the unconverted cyclohexane). The working up and distillation are carried out in the same way in Examples 14 and 15. Each of the reactors is provided with a circulation pipe which has a height of 9 m and a diameter of 1.1 m and is arranged 1.0 m above the base of the reactor. The air and the cyclohexane are fed in from below via two concentric pipes. 80 tonnes/hour are pumped into the oxidation system, 0.3 ppm of Co in the form of the ethylhexanoate being added to the cyclohexane upstream of each reactor. The reactor temperature is 150° C. or 145° C., measured in the lower part of the particular reactor, and the reaction pressure is 16 bar. 1,000 m$^3$(S.T.P.)/hour of air are fed into each reactor, the gas emerging at a velocity of 0.03 m/sec. After the working up procedure, the yield of cyclohexanone and cyclohexanol is 81.2 mol %, based on converted cyclohexane.

EXAMPLE 15

The same oxidation system is provided with a gas distributor which uniformly distributes the air over the reactor cross-section and the reactor height. The liquid content is gassed at 7 levels 2 m apart. In order to reduce back-mixing, perforated sheets (100 mm × 40 mm diameter) which have a free area of 7%, based on the reactor cross-section, are incorporated in each reactor, below the gas distributor. The gas distributor for each level is designed so that the air emerges underneath the gassing tube (nominal diameter 32), through 33 holes of 3 mm diameter which are distributed uniformly over the reactor cross-section. Each hole is provided with an enveloping tube of 60 mm length and 25 mm diameter. The velocity with which the gas emerges under operating conditions is 0.001 m/sec. As in Example 14, the reactor system is charged with 80 tonnes/hour of cyclohexane at 150° C. or 145° C. and under 15 bar. 1,000 m$^3$(S.T.P.)/hour of air are fed into each reactor, uniformly via the gassing apparatus. After the working up procedure, the yield of cyccohexanone and cyclohexanol is 86.5 mol %, based on converted cyclohexane.

We claim:

1. A process for the continuous preparation of cyclohexanol and cyclohexanone by oxidizing cyclohexane in the liquid phase with a gas containing molecular oxygen, at elevated temperatures and under superstmospheric pressure, wherein the said gas is fed into the liquid reaction mixture, in a downward direction, at several points along the reaction zone via nozzle apertures, so that it emerges at each nozzle aperture at a velocity of from 0.01 to 1 m/sec in an amount of from 0.001 to 10 liters per second per nozzle aperture, and the said reaction mixture is brought into substantially uniform contact with the gas containing molecular oxygen, over the volume of the reaction zone.

2. The process of claim 1, wherein the cyclohexane and the gas containing molecular oxygen are passed cocurrent with one another through the reaction zone.

3. The process of claim 1, wherein the gas containing molecular oxygen is fed to nozzle apertures which are uniformly distributed along the reaction zone at intervals of from 0.1 to 3 times the diameter of this zone, and over the cross-section of the particular reaction zone.

4. A process of claim 1, wherein the reaction zone is divided into chambers which are connected to one another.

5. The process of claim 1, wherein a cohesive gas phase does not form in the reaction zone.

* * * * *

UNITED STATES PATENT AND TRADEMARK OFFICE
CERTIFICATE OF CORRECTION

PATENT NO. : 4,587,363
DATED : May 6, 1986
INVENTOR(S) : Juergen HARTIG et al.

It is certified that error appears in the above-identified patent and that said Letters Patent is hereby corrected as shown below:

IN THE CLAIMS:

Claim 1, column 6, line 41, superst- should be

--superat- --

Signed and Sealed this

Sixth Day of January, 1987

Attest:

DONALD J. QUIGG

*Attesting Officer*  *Commissioner of Patents and Trademarks*